(12) United States Patent
Tamura

(10) Patent No.: US 6,885,727 B2
(45) Date of Patent: Apr. 26, 2005

(54) APPARATUS AND METHOD FOR MEASURING THICKNESS AND COMPOSITION OF MULTI-LAYERED SAMPLE

(75) Inventor: Koichi Tamura, Chiba (JP)

(73) Assignee: SII NanoTechnology Inc., Chiba (JP)

(*) Notice: Subject to any disclaimer, the term of this patent is extended or adjusted under 35 U.S.C. 154(b) by 80 days.

(21) Appl. No.: 10/213,260

(22) Filed: Aug. 6, 2002

(65) Prior Publication Data
US 2003/0031294 A1 Feb. 13, 2003

(30) Foreign Application Priority Data
Aug. 7, 2001 (JP) ......................... 2001-239216

(51) Int. Cl.⁷ ............................................. G01N 23/223
(52) U.S. Cl. ............................ 378/45; 378/46; 378/71
(58) Field of Search ............................. 378/44–50, 71

(56) References Cited
U.S. PATENT DOCUMENTS 4,959,848 A * 9/1990 Parobek ....................... 378/46
6,038,280 A * 3/2000 Rossiger et al. ............. 378/50

* cited by examiner

Primary Examiner—Craig E. Church
Assistant Examiner—Jurie Yun
(74) Attorney, Agent, or Firm—Adams & Wilks

(57) ABSTRACT

An apparatus determines the thickness and composition of a multi-layered sample comprised of at least a copper layer and a tin-copper alloy plating layer disposed on the copper layer. The sample is irradiated with primary X-rays and an energy-dispersive X-ray detector detects fluorescent X-rays and diffracted X-rays emitted from the sample. An X-ray spectrum of the detected fluorescent X-rays and diffracted X-rays is generated. The concentration of copper in the tin-copper alloy plating layer of the sample is determined utilizing peak intensities of the diffracted X-rays in the X-ray spectrum. The thickness of the tin-copper alloy plating layer of the sample is determined utilizing peak intensities of the fluorescent X-rays in the X-ray spectrum and the determined copper concentration.

12 Claims, 1 Drawing Sheet

APPARATUS AND METHOD FOR MEASURING THICKNESS AND COMPOSITION OF MULTI-LAYERED SAMPLE

BACKGROUND OF THE INVENTION

1. Field of the Invention

The present invention relates to an apparatus for simultaneously determining the thickness and composition of a multi-layered sample in a nondestructive manner and, more particularly, to an X-ray coating thickness gauge for measuring an alloy plating layer thickness and copper concentration without being influenced by the material itself when the sample to be measured is a tin-copper alloy plating layer provided on a copper alloy material.

2. Description of the Related Art

Fluorescent X-ray thickness measuring devices by which fluorescent X-rays are acquired from a multilayer sample using an X-ray generator and an energy dispersive type X-ray detector, with a layer thickness and an alloy composition then being measured using a calibration curve method or a theoretical calculation method, are well known and are widely used in determining the thickness and composition of solder, for example.

In recent years, the development of lead-free solder has been progressing due to demands for environmentally friendly products. One of these has been the development and use of tin-copper alloy plating or tin-silver-copper alloy plating, with the thickness and management composition of these platings being requested by quality A method for measuring alloy plating thickness and composition using X-ray fluorescence techniques is disclosed, for example, in Japanese Patent Laid-open No. Sho. 61-84511. This method is described simply in the following as an example applied to measuring a sample of tin-copper alloy plating.

When X-rays from an X-ray generator irradiate the sample, tin fluorescent X-rays (hereinafter referred to as Sn—K X-rays) and copper fluorescent X-rays (hereinafter referred to as Cu—K X-rays) are emitted from the tin and the copper within the alloy plating.

At this time, an intensity NS of the Sn—K X-rays and an intensity NC of the Cu—K X-rays increase as the thickness of the alloy plating increases. Further, the intensity NC of the Cu—K X-ray increases as the concentration w of copper increases. This is expressed in the form of an equation in the following manner.

$NS = f(t, w)$ $NC = g(t, w)$

A series of standard materials is measured in advance, parameters for these coefficients are determined, the measured intensity obtained from the as-yet unknown material is substituted so that a simultaneous equation is solved to determine the thickness of the plating and the concentration of the copper.

However, problems are encountered when measuring a sample where a tin-cooper alloy plating is applied on a copper material. Namely, when this kind of sample is irradiated with X-rays, Cu—K X-rays are emitted from the copper within the alloy plating and the copper of the material. When the thickness of the alloy plating increases, the intensity of the Cu—K X-rays emitted from the copper within the alloy plating increases but the intensity of the Cu—K X-rays emitted from the copper of the material conversely reduces due to being absorbed by the plating layer. Therefore, measurement is not possible because even if a consecutive standard agent group can be measured, parameters for the relational expression may be indeterminate, and even if a parameters can be determined, the simultaneous equation cannot be solved or the calculation results are unstable.

SUMMARY OF THE INVENTION

The advantage of the present invention is to provide an X-ray coating thickness gauge capable of simultaneously measuring plating thickness and copper concentration of a sample having a tin alloy plating layer including ten percent or less copper by weight on a material constituted by one or more layers including copper.

Namely, the present invention is characterized by an X-ray coating thickness gauge comprising an X-ray generator for generating primary X-rays, a collimator for allowing part of luminous flux of the primary X-rays to pass and only allowing very snail area of the sample to be measured to be irradiated with X-rays, an energy-dispersive X-ray detector for detecting secondary X-rays from the sample to be measured and a counting circuit for acquiring a signal from the detector and counting the intensity for each energy. Here, when the sample to be measured is a tin alloy plating layer including ten percent or less copper by weight on a material constituted by one or more layers including copper, the copper concentration of the tin alloy plating layer is determined using the intensity of peaks caused by diffracted X-rays in X-ray spectra information acquired by the count circuit.

When the sample to be measured is irradiated with primary X-rays, fluorescent X-rays peculiar to the elements included in the sample to be measured are generated. If, at this time, the subject to be measured is crystalline, diffracted X-rays are also generated in addition to the fluorescent X-rays.

Taking a lattice constant for crystalline matter to be d, and an X-ray wavelength to be $\lambda$, diffraction X-rays are generated based on an angle $\theta$ fulfilling the Bragg equation:

$n\lambda = 2d \sin \theta$ (where n is a natural number).

In other words, when the angle made by the X-ray generator—sample to be measured—detector is $2\theta$, if the primary X-rays are white X-rays, then X-rays of a wavelength satisfying the Bragg equation are incident to the detector.

This is then detected by the energy-dispersive detector, and peaks are observed for diffraction X-rays other than fluorescent X-rays in X-ray spectra obtained by counting the number of X-ray photons for each energy using the counter circuit.

When tin alloy plating including ten percent or less by weight of copper is then formed, an intermetallic compound of a certain ratio of $Sn_6Cu_5$ and $Sn_3Cu$ is formed. These intermetallic compounds are crystalline and have characteristic lattice constants. Diffracted X-rays are therefore generated when the tin-copper alloy is irradiated with primary X-rays. On the other hand, when the tin-copper alloy plating sample is irradiated with primary X-rays, the intensity of the diffracted X-rays generated is not particularly influenced by the thickness in the range of 1 to 10 $\mu$m used as plating and the concentration of copper is therefore well reflected. Further, the intensity of the diffracted X-rays is not subjected to the influence of the plating material.

The concentration of copper in the tin-copper alloy plating layer can then be determined by irradiating the tin-copper alloy plating material with primary X-rays to acquire X-ray spectra and using the peak intensities of the diffracted X-rays derived from the tin-copper intermetallic compound. In order to achieve this, a standard tin-copper agent of a known copper concentration may be measured at several points so as to produce a calibration curve.

The intensity of the Sn—K X-rays can also be obtained because there are tin fluorescent X-ray peaks (Sn—K X rays) in the attained X-ray spectra and the thickness of the alloy plating can therefore be measured by carrying out correction using information regarding copper concentration obtained in advance.

As described above, the copper concentration can first be determined from a single acquired X-ray spectra using the intensity of the diffracted X-rays and the thickness of the plating can be determined from the copper concentration information and the intensity of the fluorescent X-rays.

DETAILED DESCRIPTION OF THE PREFERRED EMBODIMENT

Figure 1:
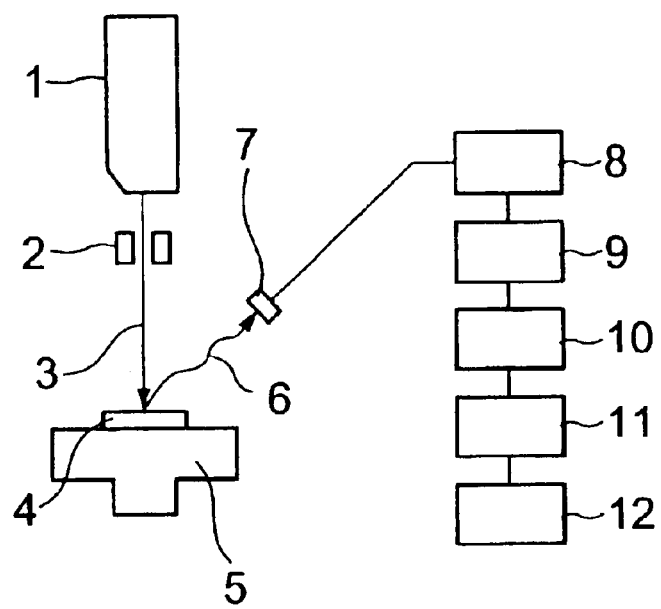
FIG. 1 is a schematic view showing an X-ray coating thickness gauge according to an embodiment of the present invention.
Figure 2:
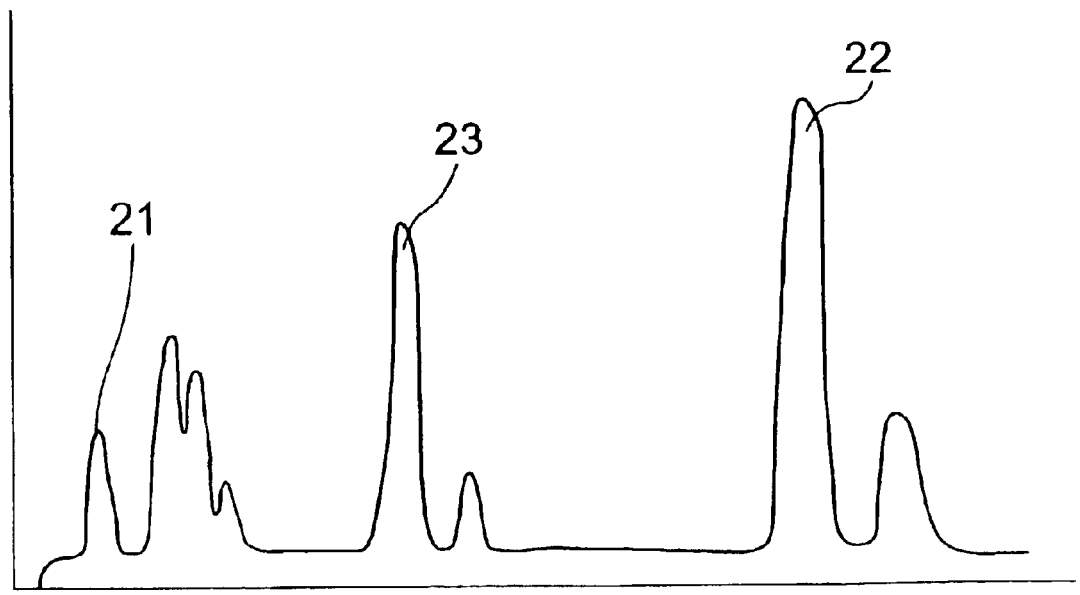
FIG. 2 shows an example of an X-ray spectrum obtained by the X-ray coating thickness gauge of the present invention.

The following is a description, with reference to FIG. 1 and FIG. 2, of a preferred embodiment of the present invention.

FIG. 1 is a schematic view showing an X-ray coating thickness gauge constituting an embodiment of the present invention. In this embodiment, primary X-rays 3 emitted by an X-ray tube 1 are focused by a collimator 2 and irradiated onto a microacopic part of a sample 4 supported by a holder 5 and comprised of a tin-copper alloy plating layer disposed on a copper layer or on a film including at least the copper layer. Fluorescent X-rays and, diffracted X-rays 6 are emitted from the tin-copper alloy plating sample 4 and are detected by a detector 7.

In this embodiment, a counting circuit comprises a linear amplifier 9 and a pulse height discriminator 10. The detected signal is then amplified by a preamplifier 8 and the linear amplifier 9 before being energy resolved at the pulse height discriminator 10. Spectral information is then created by a CPU 11 and displayed as a spectrum at a display unit 12.

An example of an X-ray spectrum obtained at this time is shown in FIG. 2. A peak is also observed for diffracted X-rays 21 coming from the tin-copper plating in addition to the fluorescent X-rays (Sn—K X-rays) 22 from the tin and the fluorescent X-rays (Cu—K X-rays) 23 from the copper.

The peak intensity of the diffracted X-rays 21 reflect copper concentration and a calibration curve can therefore be made by measuring standard materials of a known a copper concentration in advance. The copper concentration of the tin-copper alloy plating sample 4 is determined using the peak intensity of the diffracted X-rays and the calibration curve by a concentration determining means.

Further, the thickness of the plating can be measured using Sn—K X-rays and a calibration circle can therefore be made by measuring standard materials of known thicknesses. The thickness of the tin-copper alloy plating sample 4 is determined using the peak intensity of Sn—K X-rays and the calibration curve by a thickness determining means.

In this embodiment, the CPU 11 has the concentration determining means and the thickness determining means.

The unknown material is then measured and the copper concentration and plating thickness are determined using the respective calibration curves.

According to the present invention, in the measurement of the thickness and copper concentration of tin alloy plating layers including copper of ten percent by weight or less employing an X-ray thickness measurer, the copper concentration can be determined from a single obtained X-ray spectrum using diffracted X-ray intensity, and the copper concentration can therefore be determined without being influenced by the plating thickness or without being influenced by the material. It is also then possible to determine the plating thickness from the information determined for the copper concentration and from the intensity of the fluorescent X-rays.

What is claimed is:

1. An apparatus for measuring the thickness and composition of a multi-layered sample, the apparatus comprising:

an X-ray generator for generating primary X-rays;

a sample holder for supporting a sample having a tin-copper alloy plating layer disposed on a film comprised of one or more layers including at least a copper layer;

a collimator for focusing primary X-rays generated by the X-ray generator and allowing part of a luminous flux of the primary X-rays to irradiate onto a microscopic area of the sample so that fluorescent X-rays and diffracted X-rays are emitted from the sample;

an energy-dispersive X-ray detector for detecting the fluorescent X-rays and diffracted X-rays emitted from the sample; and means for generating an X-ray spectrum of the fluorescent X-rays and diffracted X-rays detected by the energy-dispersive X-ray detector, measuring the concentration of copper in the tin-copper alloy plating layer of the sample using peak intensities of the diffracted X-rays in the X-ray spectrum, and measuring the thickness of the tin-copper alloy plating layer of the sample using peak intensities of the fluorescent X-rays in the X-ray spectrum and the measured concentration of copper.

2. An apparatus for measuring the thickness and composition of a multi-layered sample, the apparatus comprising:

an X-ray generator for generating primary X-rays;

a sample holder for supporting a sample comprised of a tin-copper alloy plating layer disposed on a film having one or more layers including at least a copper layer;

a collimator for focusing primary X-rays generated by the X-ray generator and allowing part of a luminous flux of the primary X-rays to irradiate onto a microscopic area of the sample so that fluorescent X-rays and diffracted X-rays are emitted from the sample;

an energy-dispersive X-ray detector for detecting the fluorescent X-rays and diffracted X-rays emitted from the sample; and means for generating an X-ray spectrum of the fluorescent X-rays and diffracted X-rays detected by the energy-dispersive X-ray detector, for measuring the concentration of copper in the tin-copper alloy plating layer of the sample using peak intensities of the diffracted X-rays in the X-ray spectrum, for measuring the thickness of the tin-copper alloy plating layer of the sample using peak intensities of the fluorescent X-rays in the X-ray spectrum and the measured concentration of copper, and for measuring the concentration of elements and the thickness of one or more of the film layers of the sample in accordance with the X-ray spectrum.

3. An apparatus according to claim 1; wherein the tin-copper alloy plating layer contains ten percent or less copper by weight.

4. An apparatus according to claim 2; wherein the tin-copper alloy plating layer contains ten percent or less copper by weight.

5. An apparatus for determining the thickness and composition of a multi-layered sample, the apparatus comprising:

an X-ray generator for generating primary X-rays;

sample holding means for holding a multi-layered sample at a position such that the sample will be irradiated by the primary X-rays generated by the X-ray generator, the sample having at least a copper layer and a tin-copper alloy plating layer disposed on the copper layer;

an energy-dispersive X-ray detector for detecting fluorescent X-rays and diffracted X-rays emitted from the sample when the sample is irradiated by the primary X-rays generated by the X-ray generator;

generating means for generating an X-ray spectrum of the fluorescent X-rays and diffracted X-rays detected by the energy-dispersive X-ray detector;

concentration determining means for determining the concentration of copper in the tin-copper alloy plating layer of the sample utilizing peak intensities of the diffracted X-rays in the X-ray spectrum; and thickness determining means for determining the thickness of the tin-copper alloy plating layer of the sample utilizing peak intensities of the fluorescent X-rays in the X-ray spectrum and the concentration of copper determined by the concentration determining means.

6. An apparatus according to claim 5; wherein the tin-copper alloy plating layer of the sample contains ten percent or less copper by weight.

7. An apparatus according to claim 5; wherein the sample has a multi-layered film including the copper layer, the tin-copper alloy plating layer being disposed on the multi-layered film.

8. An apparatus according to claim 5; wherein the generating means comprises a central processing unit for generating spectral information of the fluorescent X-rays and diffracted X-rays and a display unit for displaying the spectral information as the X-ray spectrum.

9. A method for determining the thickness and composition of a multi-layered sample, the method comprising the steps of:

providing a sample comprised of at least a copper layer and a tin-copper alloy plating layer disposed on the copper layer;

irradiating the sample with primary X-rays;

detecting fluorescent X-rays and diffracted X-rays emitted from the sample due to irradiation of the sample with the primary X-rays;

generating an X-ray spectrum of the detected fluorescent X-rays and diffracted X-rays;

determining the concentration of copper in the tin-copper alloy plating layer of the sample utilizing peak intensities of the diffracted X-rays in the X-ray spectrum; and determining the thickness of the tin-copper alloy plating layer of the sample utilizing peak intensities of the fluorescent X-rays in the X-ray spectrum and the determined copper concentration.

10. A method according to claim 9; wherein the tin-copper alloy plating layer of the sample contains ten percent or less copper by weight.

11. A method according to claim 9; wherein the sample comprises a multi-layered film including the copper layer, the tin-copper alloy plating layer being disposed on the multi-layered film.

12. A method according to claim 9; wherein the generating step includes the steps of generating spectral information of the fluorescent X-rays and diffracted X-rays and displaying the spectral information as the X-ray spectrum.

* * * * *